United States Patent
Ward

(10) Patent No.: US 6,845,568 B2
(45) Date of Patent: Jan. 25, 2005

(54) HIGH PERFORMANCE FOOT BED FOR SPORTS EQUIPMENT

(76) Inventor: Eric G. Ward, P.O. Box 2574, Aspen, CO (US) 81612

( * ) Notice: Subject to any disclaimer, the term of this patent is extended or adjusted under 35 U.S.C. 154(b) by 0 days.

(21) Appl. No.: 10/389,435

(22) Filed: Mar. 14, 2003

(65) Prior Publication Data

US 2003/0213138 A1 Nov. 20, 2003

Related U.S. Application Data

(63) Continuation-in-part of application No. 09/667,998, filed on Sep. 22, 2000, now Pat. No. 6,564,465.

(51) Int. Cl.$^7$ ............................................. A61B 5/103
(52) U.S. Cl. .......................... 33/515; 33/3 R; 600/592; 12/1 G; 12/142 R
(58) Field of Search ........................... 33/515, 511, 512, 33/2 R, 3 R, 6, 3 A, 3 C, 3 B; 600/592; 12/1 R, 1 G, 142 R

(56) References Cited

U.S. PATENT DOCUMENTS

| | | | | |
|---|---|---|---|---|
| 3,375,586 A | * | 4/1968 | Kennedy | ...................... 33/3 R |
| 4,917,105 A | * | 4/1990 | Tiitola et al. | .................. 33/515 |
| 5,168,634 A | * | 12/1992 | Misevich | ...................... 33/515 |
| 5,822,873 A | * | 10/1998 | Meilman | ...................... 33/365 |
| 5,979,067 A | * | 11/1999 | Waters | ......................... 33/512 |
| 6,160,264 A | * | 12/2000 | Rebiere | ....................... 33/515 |
| 6,219,929 B1 | * | 4/2001 | Tasker et al. | ................. 33/515 |
| 6,564,465 B1 | * | 5/2003 | Ward | ............................ 33/515 |

* cited by examiner

Primary Examiner—Christopher W. Fulton
(74) Attorney, Agent, or Firm—Niro, Scavone, Haller & Niro

(57) ABSTRACT

A system for creating at least one foot insert for an individual using a neutralizer 10, a levelor 40, and a sled 60. The neutralizer has a housing, protractor, and an angularly adjustable plate capable of supporting the foot. The neutralizer is adapted to accommodate a single foot of the individual to determine the neutral angle for each foot individually. The levelor is positionable on the neutralizer and has a plurality of adjustable arms to transfer the neutral angle from the neutralizer to the levelor. The levelor is also mountable to the sled with the adjustable arms being adapted to engage an insert for transferring the neutral angle to the insert.

3 Claims, 3 Drawing Sheets

HIGH PERFORMANCE FOOT BED FOR SPORTS EQUIPMENT

This application is a CIP of U.S. application Ser. No. 09/667,998 filed Sep. 22, 2000, now U.S. Pat. No. 6,564,465.

BACKGROUND OF THE INVENTION

The present invention relates to a device and method for forming an athletic foot support that may be used in such equipment as, among other things, ski boots, skates, bike shoes and the like. More specifically, the present invention concerns a device and method that produces an insert or foot support that positions the ankle joint or sub taylor joint in a relaxed position by correcting the pronation of the foot.

SUMMARY OF THE INVENTION

This invention provides a device and method that measures and then corrects the pronation of the foot, a condition where the foot collapses to the medial or inside of the foot, and how this affects athletic ability. The degree of pronation is evaluated for each foot independently. The end result provides an equal amount of pronation to occur in each foot by building a corrective mold of the foot, or a "canted footbed". Being that most individual's feet have individual needs, it is critical to evaluate each foot separately. This is important to many athletic activities that demand the athlete to move symmetrically—for instance, skiing, skating, and any other laterally-oriented sport. The term "canted footbed" like a house, provides a solid level object for the house to sit upon. The foot bed is the foundation for the muscular-skeletal system to sit upon and work most efficiently since the foot is a complex joint. Not only does it support enormous amounts of weight, but it is the primary joint for balancing. The present invention is a process and device that takes both of these factors into consideration. The foot must be able to support the weight of the body plus the added weight of G forces, especially in skiing. While supporting large loads, it must also be able to make fine-tuning movements while skiing. Understanding the demands of skiing specifically was the thrust behind the invention. The physics of the sport require that the skier balance on top of a frictionless surface while moving dynamically from one foot to the other. Symmetric movement is important in the creation of a seamless move from one side to the other with rhythmic flow. If the sub taylor joint is predisposed with nonfunctional tension, the ability to move freely will be jeopardized. The fine muscular movements of the foot and ankle dictate the degree of success in the rest of the biomechanical chain. This is, to a large extent, the cause of tension or an imbalanced interaction in the chain.

To achieve the proper pronation of the sub taylor joint, how the foot is designed to support weight, and walk must be understood, or what is commonly referred to as a dynamic gate. The phases of the dynamic gate are heel strike, mid range, and toe off.

In the heel strike, the calcaneus hits the ground usually to the lateral side of the foot. Then the hips move forward and the weight moves to the outer three metatarsals to support lateral balance. This is known as the midrange. Then, the foot naturally pronates to one degree or another to allow the weight to move to the medial side of the foot or the two strong toes. Then, as the hips pass in front of the foot, the large strong toes will push off. This is the understanding of the dynamics of the foot in a stride.

In skiing, biking, skating, etc . . . because the equipment limits the range of motion, there is no stride, there is only lateral movement—basically, stuck in the midrange mode. It is however a dynamic stance, because the foot moves laterally to create balance while the body is in motion. This is the difference between what the present invention achieves and what many others do in this field. All other alignment processes implement a two-footed stance to determine the position of neutrality. This is done by aligning the center of the knee in relation to the center of support. This is done while standing on two feet or in a static state. If a person is standing on two feet, you then have to look at the base of support as being a six piece balancing system. In this situation, the person may be maintaining balance equally in all six quadrants or in one of the six quadrants and using two others to maintain a steady or "static" balance.

If you reduce the base of support to only one foot, you have a three-sided base which needs to articulate to maintain balance or balance dynamically. The present invention achieves this state by first analyzing the ankle joint to determine correct foot alignment. The balance analyser and the foot level control quality and assure accuracy of the foot foundation used in the insert. Typically, the optimal outcome should be to limit the amount of pronation in the ankle to approximately two degrees. The application of this type of process to foot beds will increase the amount of relatedness in the foot and ankle joint. The subsequent outcome will be more athleticism in the user. The position of the foot will provide an ability for the user to move the foot laterally and with a great deal of agility.

BRIEF DESCRIPTION OF THE DRAWINGS

The novel features which are characteristic of the present invention are set forth in the appended claims. The invention itself, however, together with further objects and attendant advantages, will be best understood by reference to the following description taken in connection with the accompanying drawings in which:

DESCRIPTION OF THE PREFERRED EMBODIMENTS

Set forth below is a description of what is currently believed to be the preferred embodiment or best example of the invention claimed. Future and present alternatives and modifications to the preferred embodiment are contemplated. Any alternates or modifications in which insubstantial changes in function, purpose, structure or result are intended to be covered by the claims of this patent.

Figure 1:
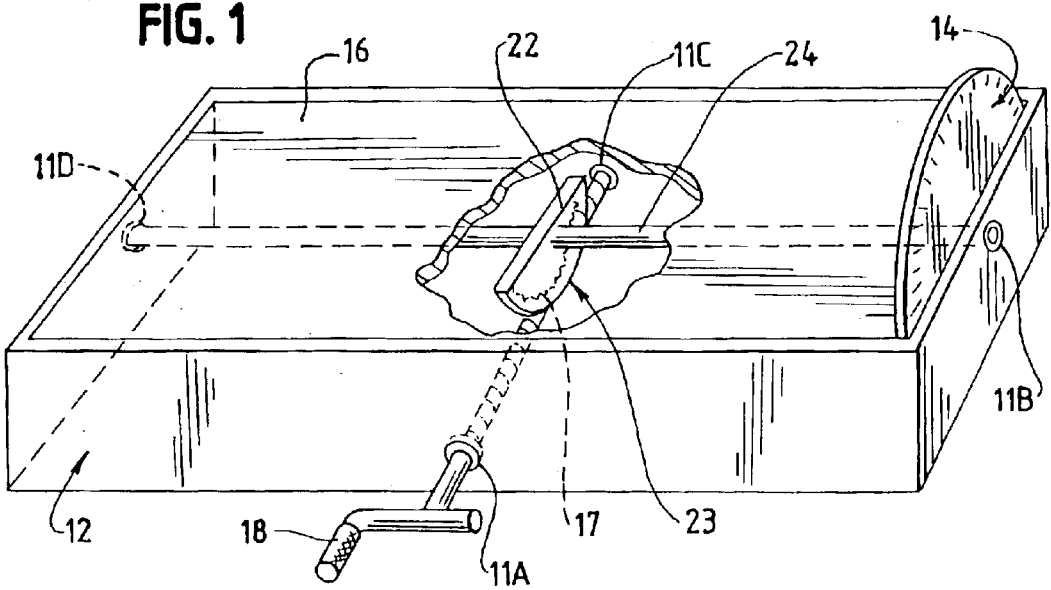
FIG. 1 shows a perspective view of one embodiment of a foot neutralizer used with the present invention.
Figure 4:
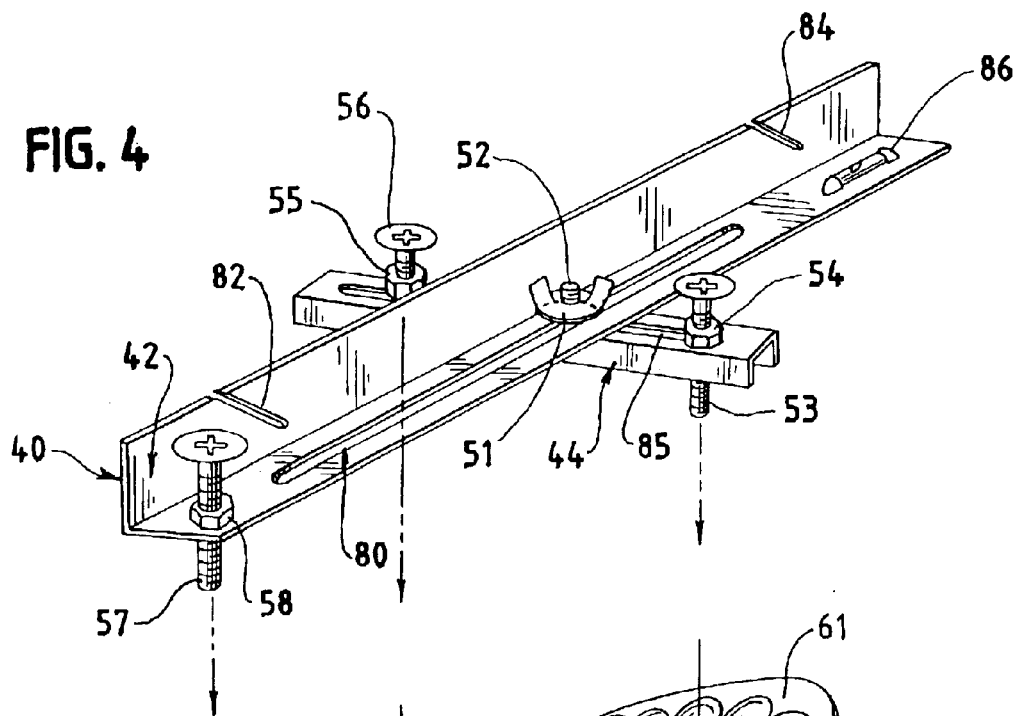
FIG. 4 is a perspective view of a leveler used with the present invention.
Figure 5:
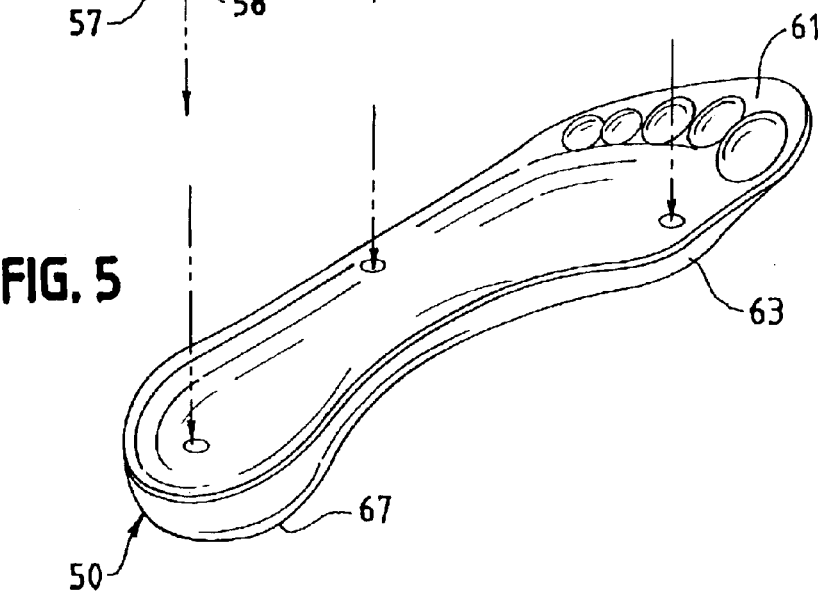
FIG. 5 is a perspective view of an insert used with the present invention.
Figure 6:
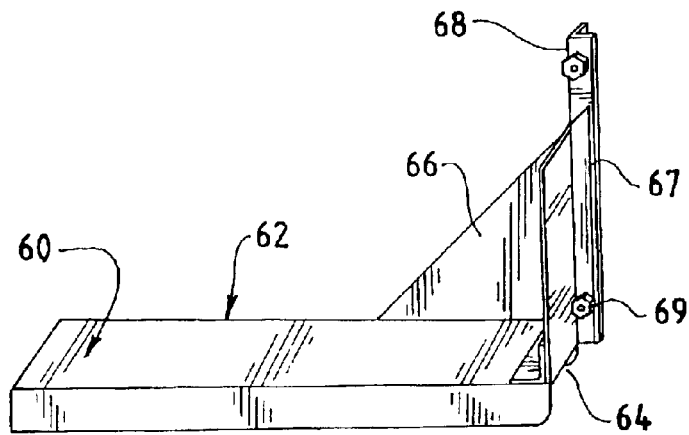
FIG. 6 is a perspective view of a jig used with the present invention.
Figure 7:
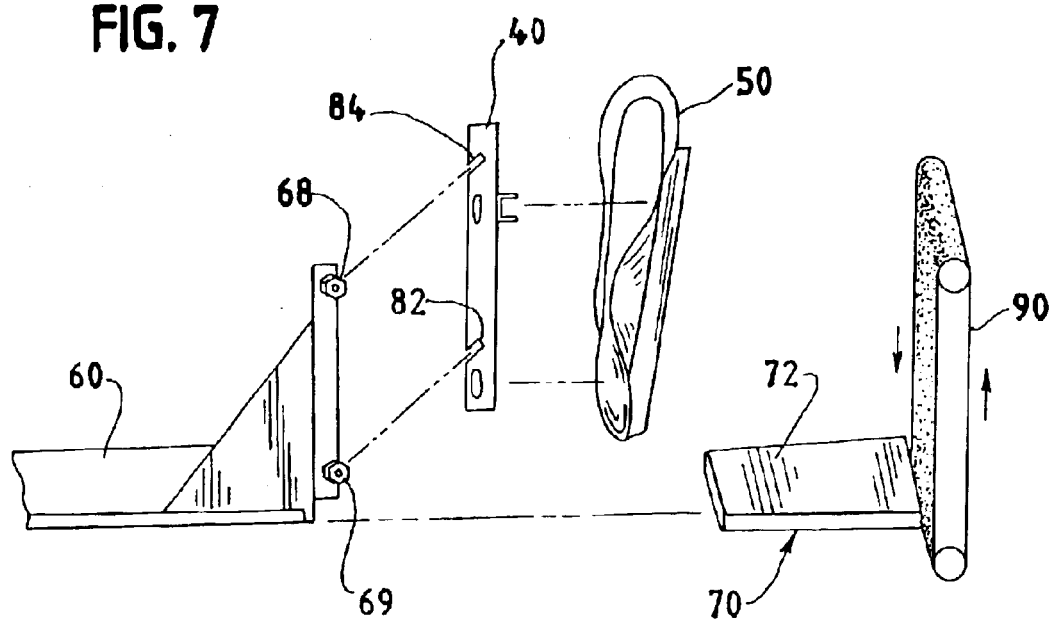
FIG. 7 is an exploded perspective view illustrating various manufacturing steps used with one embodiment of the invention.

The present invention includes a number of components such as a foot neutralizer 10 as shown in FIG. 1, a leveler 40 as shown in FIG. 4, a foot bed 50 as shown in FIG. 5, a sled 60 as shown in FIG. 6, and a sander 70 as shown in FIG. 7. Neutralizer 10 includes a housing 12, protractor 14, an angularly adjustable plate 16, crank 18 with threaded rod 19 having threads 23 that coact with threads 21 on support 22, and rod 24. Bearings 11A, 11B, 11C and 11D may also be provided for ease of operation.

Figure 2:
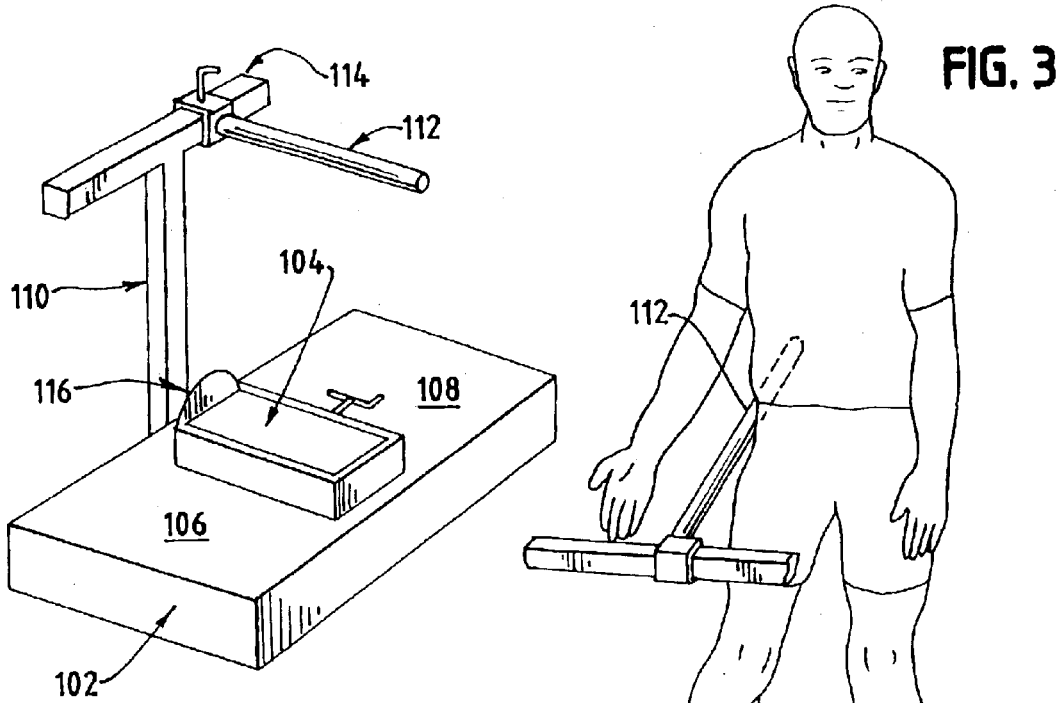
FIG. 2 shows a perspective view of an alternate embodiment of a foot neutralizer which may be used with the present invention.

FIG. 2 shows an alternate embodiment of a foot neutralizer 100. It includes a housing 102, angularly adjustable plate 104, foot rests 106 and 108, upright support bar 110, and a positionable horizontal bar 112 that adjustably slides along bar 114 of support 110. Also included is protractor 116.

Leveler 40 includes arm 42, which may be made from a piece of angle iron, and arm 44, which may be made from a unshaped channel. As shown in FIG. 4, arms 42 and 44 are generally disposed in a perpendicular relationship. Included on arm 42 are slanted notches 82 and 84 and extended groove 80. A two-way bubble indicator 86 is located on one end of arm 42. Indicator 86 may be comprised of tubing that encloses liquid and an air bubble.

Also provided on leveler 40 are a number of coacting fasteners 51–58. Fastener 52 may be a wing nut which coacts with fastener 51 which is located inside groove 80. This arrangement allows the overall length of the leveler to be adjusted to accommodate various foot sizes. Fasteners 53–56 are used to adjust the width of the leveler by being adjustable within groove 85. These fasteners along with fasteners 57 and 58 are also used to level the leveler as will be described in further detail below.

Also included with the present invention is a composite foot bed 50. It consists of a foot blank 51 which is molded to conform to the shape of the user's foot. A posting foam 53 is used as the base of the foot bed composite.

A sled 60 is also used with the present invention. It includes a base 62 defining a channel 64. Also included is upright post 67 which is supported by bracket 66.

Locking posts 68 and 69 are also provided. The locking posts function to connect the leveler to the sled. Locking posts 68 and 69 may be coacting fasteners or other clamping and locking devices.

A table 70 is also used which is adjacently located near a vertical sander. Table 70 includes a guide 72 which is sized to fit within channel 64 of sled 60. Guide 72 and channel 64 are sized within a close tolerance so as to maintain a straight line as sled 60 moves along guide 72 as will be described in more detail below.

In use, a mold is first made for each foot of the individual. This may be done by a silicon bean bag on which a foot is placed. Air is then vacuumed out of the bag so that the shape of the impression is maintained. A plaster mold is made of the impression and then a plastic mold is made over the plaster mold to form foot blank 61 of composite foot bed 50. This is done by trimming blank 61 and attaching it to posting foam 63 by adhesives. As shown in FIG. 5, when this process is finished, foot bed 60 should consist of a foot blank 61 that conforms to a user's foot which has been attached to a base 63 made of posting foam, which has a flat surface 67.

Next, leveler 40 is positioned on the foot bed. This is done by placing fastener 57 near what would be the heel portion of the foot bed at the center line. Fasteners 56 and 53 are then placed at the outer edges of bed 50 near the toe line. For reference purposes, to relocate the leveler on bed 50 for use in later finishing steps, reference marks may be made on bed 50 by a common marker. With the leveler 40 at rest on bed 50, the lengths of fasteners 53, 56 and 57 are adjusted to level leveler 40 on bed 50 through the use of bubble level 86.

To determine an individual's neutral ankle position, foot neutralizer 10 or 100 is used. To determine a neutral position, one foot at a time is measured, while maintaining an individual in the same upright, relaxed stance. To do this, for an individual's left foot, the person stands on foot neutralizer 100. The left foot is placed on plate 104 which is in a level position and the right foot is placed on rest 108. The individual then stands upright in a relaxed position and may use bar 114 for support. Wand or bar 112 is located next to the person's hip which acts as reference point for maintaining this position.

The heel of the foot is placed on the center line which is defined by rod 24. Crank 18 is then operated by rotation which causes threads 21 and 23 to coact thereby resulting in plate 16 being angularly adjusted. Protractor 14 indicates the amount of adjustment undertaken. The same type of adjustment system is also used with the neutralizer shown in FIG. 2.

Figure 3:
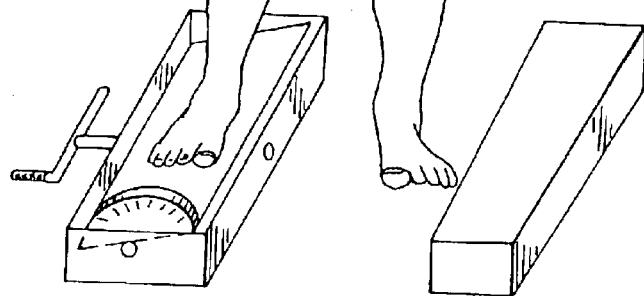
FIG. 3 illustrates how the foot neutralizer shown in FIG. 1 is used to take a pronation measurement.

To achieve a neutral position, the operator visually examines the tendons by the ankle until they are in a relaxed state or are working equally. This commonly occurs with no more than two degrees of adjustment of pronation—with the big toe of the foot over the smaller toes as shown in FIG. 3. However, supination, orientation with smaller toes over the big toe, may also occur.

Next the adjustment plate is left at the angular orientation selected and may be locked in place. Leveler 40 is then placed on plate 16 or 104 in approximately the same location as was the foot. The lengths of fasteners 53, 56 and 57 are then adjusted to level leveler 40 by observing bubble levels 86. It should be noted that fasteners 54, 55 and 58 may be a double nut arrangement which assists in maintaining the desired location and length of the fasteners.

Next, leveler 40 is placed on foot bed 50 in the same position in which it was originally adjusted to level. Bed 50 and leveler 40 are then secured together by masking tape or other suitable means. Through this process, the angle of plate 16 or 104 as measured by the protractor will be transferred to bed 50.

As shown in FIG. 7, leveler 40 is mounted to sled 60. This is done by inserting grooves 82 and 84 onto locking knobs or posts 68 and 69 which are sized to fit inside of the grooves. Sander 90 is then activated and is used to remove the flat surface 67 of bed 50.

To do this sled 60 is mounted on table 70 by placing guide 72 inside channel 64. This allows surface 67 of bed 50 to be urged against sander 90 which removes the foam of bed 50 to reproduce the same angle as that of plate 16 or 104. Once the sander has removed a sufficient amount of material along the entire length and width of bed 50, the process is completed. To perform the process for the other foot, the exact some procedure is used.

Figure 8:
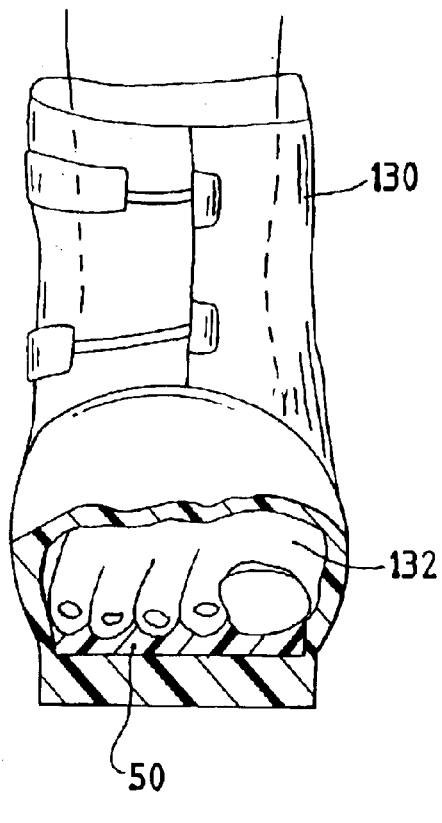
FIG. 8 is a front view showing an insert located in a ski boot.
Figure 9:
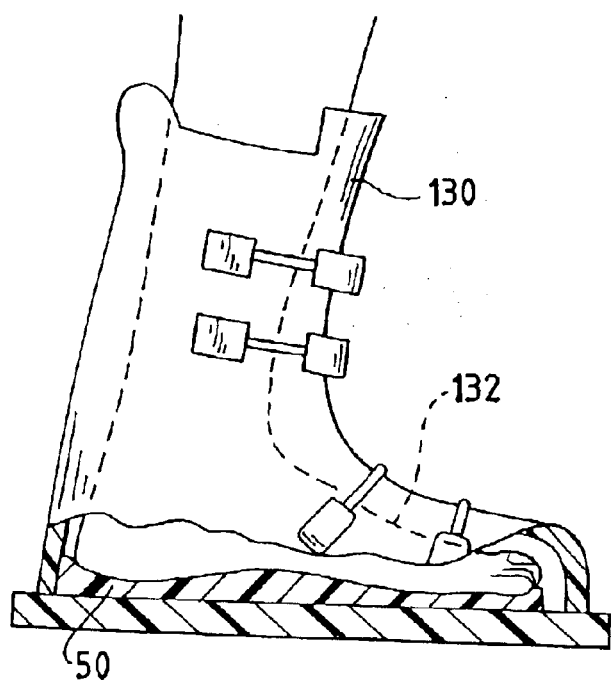
FIG. 9 is a side view showing an insert in a ski boot.

As shown in FIGS. 8 and 9, bed 50 is placed inside a piece of sports equipment such as ski boot 130. As shown, bed 50 holds foot 132 at the angle which is the neutral state for the ankle. Of course, as mentioned above, bed or insert 50 may be used in other sports equipment as well.

In addition, the inserts 50 may be pre-made with a range of predetermined angles. For example, insert 50 may have an angle that ranges from ½ a degree to 3 degrees and be pre-made in ½ degree increments. This reduces the turn-around time to complete the process.

It should be understood that various changes and modifications to the preferred embodiment described would be apparent to those skilled in the art. Changes and modifications can be made without departing from the spirit and scope of the present invention and without diminishing its intended advantages. It is, therefore, intended that such changes and modifications be covered by the following claims.

What is claimed is:

1. A method of fitting an individual with right and left foot inserts which place the ankles of the individual in a neutral position comprising the steps of:

for creating a right foot insert, having the individual place the right foot on a neutralizer while elevating the left foot off of the neutralizer;

using the neutralizer to determine the angle necessary to place the right ankle in a neutral position;

providing an insert having an angle which represents the neutral state for the right ankle;

for creating a left foot insert, having the individual place the left foot on a neutralizer while elevating the right foot off of the neutralizer;

using the neutralizer to determine the angle necessary to place the left ankle in a neutral position; and providing an insert having an angle which represents the neutral state for the left ankle.

2. The method of claim 1 further comprising the step of making said insert conform to the foot of the user.

3. The method of claim 1 wherein said insert is provided to a user by selecting said insert from a plurality of predetermined inserts.

* * * * *